United States Patent
DiMeo et al.

(10) Patent No.: US 8,808,241 B2
(45) Date of Patent: Aug. 19, 2014

(54) RAPID FLUID COOLING DEVICES AND METHODS FOR COOLING FLUIDS

(71) Applicant: North Carolina State University, Raleigh, NC (US)

(72) Inventors: Andrew J. DiMeo, Raleigh, NC (US); Nathan M. Cox, Raleigh, NC (US); Steven P. Grove, Mooresville, NC (US); Samuel Lee, Raleigh, NC (US); Luke D. Oltmans, Raleigh, NC (US); Kathryn H. Sauer, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 14/054,315

(22) Filed: Oct. 15, 2013

(65) Prior Publication Data

US 2014/0046257 A1    Feb. 13, 2014

Related U.S. Application Data

(62) Division of application No. 12/711,749, filed on Feb. 24, 2010, now Pat. No. 8,608,696.

(60) Provisional application No. 61/154,972, filed on Feb. 24, 2009.

(51) Int. Cl.
| | |
|---|---|
| *A61F 7/12* | (2006.01) |
| *A61F 7/00* | (2006.01) |
| *A61M 5/44* | (2006.01) |
| *A61F 7/10* | (2006.01) |
| *A61F 7/02* | (2006.01) |

(52) U.S. Cl.
CPC ............... *A61M 5/44* (2013.01); *A61F 7/0085* (2013.01); *A61F 7/106* (2013.01); *A61F 2007/0276* (2013.01)
USPC ........................................................ 604/113

(58) Field of Classification Search
CPC .......... A61M 5/44; A61M 2205/3368; A61M 2205/127; A61M 2205/3606; A61M 1/36; A61M 2205/3372; A61M 1/3621; A61B 18/02; A61B 18/18; A61B 2017/00106; A61B 2018/0212; A61B 17/8816; A61B 17/8836
USPC .............................................. 604/87–89, 113
See application file for complete search history.

(56) References Cited

U.S. PATENT DOCUMENTS 4,065,235 A * 12/1977 Furlong et al. ................ 417/420
4,522,640 A    6/1985 Jagoe, III (Continued)

FOREIGN PATENT DOCUMENTS

| AU | 199946852 B2 | 1/2000 |
|---|---|---|
| AU | 2007201161 A1 | 4/2007 |

(Continued)

OTHER PUBLICATIONS

Hypothermia after Cardiac Arrest Study Group, (2002), Mild therapeutic hypothermia to improve the neurologic outcome after cardiac arrest. The New England Journal of Medicine, 346(8), 549-556.

(Continued)

*Primary Examiner* — Nicholas Lucchesi
*Assistant Examiner* — Diva K Chander
(74) *Attorney, Agent, or Firm* — Olive Law Group, PLLC

(57) ABSTRACT

A cooling device includes a target fluid inlet, a target fluid outlet, an inner conduit, and a chamber surrounding the inner conduit. The inner conduit communicates with the target fluid inlet and the target fluid outlet, and provides a flow path for a target fluid to be cooled. The chamber contains a first endothermic reactant and includes a reactant inlet selectively alterable from a closed state to an open state. When the reactant inlet is in the closed state, the first endothermic reactant is isolated from a second endothermic reactant and no endothermic reaction occurs. When the reactant inlet is in the open state, the reactant inlet provides a flow path for enabling the second endothermic reactant to come into contact with the first endothermic reactant in the chamber for initiating the endothermic reaction and cooling the target fluid in the inner conduit.

16 Claims, 7 Drawing Sheets

(56) References Cited

U.S. PATENT DOCUMENTS

| | | | |
|---|---|---|---|
| 4,528,218 A | 7/1985 | Maione | |
| 4,653,577 A * | 3/1987 | Noda | 165/71 |
| 4,697,636 A | 10/1987 | Mellsjo | |
| 4,705,505 A | 11/1987 | Fried | |
| 4,751,119 A | 6/1988 | Yukawa | |
| 4,758,562 A | 7/1988 | Adler et al. | |
| 4,986,076 A | 1/1991 | Kirk et al. | |
| 4,993,237 A | 2/1991 | Bond et al. | |
| 5,062,269 A | 11/1991 | Siegel | |
| 5,088,302 A | 2/1992 | Tomizawa et al. | |
| 5,219,274 A * | 6/1993 | Pawlowski et al. | 417/213 |
| 5,263,929 A | 11/1993 | Falcone et al. | |
| 5,395,314 A * | 3/1995 | Klatz et al. | 604/24 |
| 5,429,762 A * | 7/1995 | Kitahara et al. | 252/70 |
| 5,494,416 A * | 2/1996 | Gergets | 417/420 |
| 5,752,929 A * | 5/1998 | Klatz et al. | 604/506 |
| 5,827,222 A * | 10/1998 | Klatz et al. | 604/507 |
| 5,840,068 A * | 11/1998 | Cartledge | 604/131 |
| 5,913,885 A * | 6/1999 | Klatz et al. | 607/104 |
| 6,019,783 A | 2/2000 | Philips et al. | |
| 6,033,383 A | 3/2000 | Ginsburg | |
| 6,035,102 A | 3/2000 | Bakke | |
| 6,042,559 A | 3/2000 | Dobak, III | |
| 6,051,019 A | 4/2000 | Dobak, III | |
| 6,056,932 A | 5/2000 | Von Hippel et al. | |
| 6,076,597 A | 6/2000 | Manning et al. | |
| 6,090,132 A | 7/2000 | Fox | |
| 6,096,068 A | 8/2000 | Dobak, III et al. | |
| 6,110,168 A | 8/2000 | Ginsburg | |
| 6,149,624 A | 11/2000 | McShane | |
| 6,149,670 A | 11/2000 | Worthen et al. | |
| 6,149,676 A | 11/2000 | Ginsburg | |
| 6,149,677 A | 11/2000 | Dobak, III | |
| 6,158,994 A * | 12/2000 | Mulcahy | 418/102 |
| 6,224,624 B1 | 5/2001 | Lasheras et al. | |
| 6,231,594 B1 | 5/2001 | Dae | |
| 6,231,595 B1 * | 5/2001 | Dobak, III | 607/106 |
| 6,233,945 B1 | 5/2001 | Kohout | |
| 6,264,679 B1 | 7/2001 | Keller et al. | |
| 6,270,324 B1 * | 8/2001 | Sullivan et al. | 417/420 |
| 6,306,161 B1 | 10/2001 | Ginsburg | |
| 6,440,158 B1 | 8/2002 | Saab | |
| 6,454,792 B1 | 9/2002 | Noda et al. | |
| 6,478,812 B2 | 11/2002 | Dobak, III et al. | |
| 6,527,798 B2 | 3/2003 | Ginsburg et al. | |
| 6,547,811 B1 | 4/2003 | Becker et al. | |
| 6,554,791 B1 * | 4/2003 | Cartledge et al. | 604/67 |
| 6,572,640 B1 | 6/2003 | Balding et al. | |
| 6,582,455 B1 | 6/2003 | Dobak, III et al. | |
| 6,607,517 B1 | 8/2003 | Dae et al. | |
| 6,620,131 B2 | 9/2003 | Pham et al. | |
| 6,623,514 B1 | 9/2003 | Chin | |
| 6,656,209 B1 | 12/2003 | Ginsburg | |
| 6,702,839 B1 | 3/2004 | Dae et al. | |
| 6,736,790 B2 | 5/2004 | Barbut et al. | |
| 6,752,786 B2 | 6/2004 | Callister | |
| 6,878,156 B1 | 4/2005 | Noda | |
| 6,905,509 B2 | 6/2005 | Dobak, III et al. | |
| 6,939,520 B2 | 9/2005 | Filippi et al. | |
| 6,962,601 B2 | 11/2005 | Becker et al. | |
| 7,008,444 B2 | 3/2006 | Dae et al. | |
| 7,008,445 B2 | 3/2006 | Lennox | |
| 7,014,651 B2 | 3/2006 | Worthen et al. | |
| 7,052,509 B2 | 5/2006 | Lennox et al. | |
| 7,077,825 B1 | 7/2006 | Stull | |
| 7,144,418 B1 | 12/2006 | Lennox | |
| 7,231,771 B2 | 6/2007 | McMurry et al. | |
| 7,303,328 B2 * | 12/2007 | Faraldi et al. | 366/101 |
| 7,311,724 B1 | 12/2007 | Ginsburg | |
| 7,350,361 B2 | 4/2008 | Maxwell et al. | |
| 7,422,600 B2 * | 9/2008 | Dobak, III | 607/105 |
| 7,422,601 B2 | 9/2008 | Becker et al. | |
| 7,449,018 B2 * | 11/2008 | Kramer | 606/21 |
| 7,507,250 B2 | 3/2009 | Lennox | |
| 7,571,621 B2 | 8/2009 | Dietschi et al. | |
| 7,597,136 B2 | 10/2009 | Kite et al. | |
| 7,758,623 B2 * | 7/2010 | Dzeng et al. | 607/105 |
| 7,806,915 B2 * | 10/2010 | Scott et al. | 607/106 |
| 7,827,815 B2 | 11/2010 | Carson et al. | |
| 7,867,266 B2 | 1/2011 | Collins | |
| 7,989,508 B2 | 8/2011 | Hecht | |
| 8,047,010 B2 | 11/2011 | Carson et al. | |
| 8,091,337 B2 | 1/2012 | Tepesch | |
| 8,100,123 B2 | 1/2012 | Belson | |
| 8,117,854 B2 | 2/2012 | Lampe et al. | |
| 8,157,794 B2 * | 4/2012 | Dobak et al. | 606/22 |
| 8,231,664 B2 | 7/2012 | Kulstad et al. | |
| 8,257,340 B2 | 9/2012 | Saab | |
| 8,308,787 B2 * | 11/2012 | Kreck | 607/105 |
| 8,343,202 B2 | 1/2013 | Magers | |
| 8,388,571 B2 * | 3/2013 | Joshi et al. | 604/85 |
| 8,388,578 B2 * | 3/2013 | Joshi et al. | 604/113 |
| 8,402,968 B2 | 3/2013 | Belson | |
| 8,409,265 B2 | 4/2013 | Keller et al. | |
| 8,439,960 B2 | 5/2013 | Burnett et al. | |
| 2001/0001830 A1 | 5/2001 | Dobak et al. | |
| 2001/0001831 A1 | 5/2001 | Dobak et al. | |
| 2001/0007951 A1 | 7/2001 | Dobak, III | |
| 2001/0016763 A1 | 8/2001 | Lasheras et al. | |
| 2002/0004675 A1 | 1/2002 | Lasheras | |
| 2002/0045852 A1 | 4/2002 | Saab | |
| 2002/0082671 A1 | 6/2002 | Magers et al. | |
| 2002/0095201 A1 | 7/2002 | Worthen et al. | |
| 2002/0111584 A1 | 8/2002 | Walker et al. | |
| 2002/0111657 A1 | 8/2002 | Dae et al. | |
| 2002/0116039 A1 | 8/2002 | Walker et al. | |
| 2002/0138122 A1 | 9/2002 | Worthen et al. | |
| 2002/0151845 A1 | 10/2002 | Werneth | |
| 2002/0151942 A1 | 10/2002 | Walker et al. | |
| 2002/0151944 A1 | 10/2002 | Pham et al. | |
| 2002/0161349 A1 | 10/2002 | Allers et al. | |
| 2002/0161351 A1 | 10/2002 | Samson et al. | |
| 2002/0183816 A1 | 12/2002 | Tzeng et al. | |
| 2002/0198579 A1 | 12/2002 | Khanna | |
| 2003/0004456 A1 | 1/2003 | Saab | |
| 2003/0060761 A1 | 3/2003 | Evans et al. | |
| 2003/0078641 A1 | 4/2003 | Dobak, III | |
| 2003/0130651 A1 | 7/2003 | Lennox | |
| 2003/0139791 A1 | 7/2003 | Dobak, III | |
| 2003/0216746 A1 | 11/2003 | Worthen et al. | |
| 2004/0073280 A1 | 4/2004 | Dae et al. | |
| 2004/0158191 A1 | 8/2004 | Samson et al. | |
| 2004/0199114 A1 | 10/2004 | Noda | |
| 2004/0199229 A1 | 10/2004 | Lasheras | |
| 2004/0210281 A1 * | 10/2004 | Dzeng et al. | 607/96 |
| 2004/0215163 A1 | 10/2004 | Walker et al. | |
| 2004/0215297 A1 | 10/2004 | Collins | |
| 2004/0220647 A1 | 11/2004 | Noda | |
| 2005/0004503 A1 | 1/2005 | Samson et al. | |
| 2005/0027244 A1 | 2/2005 | Eidenschink | |
| 2005/0027281 A1 | 2/2005 | Lennox | |
| 2005/0033391 A1 | 2/2005 | Worthen et al. | |
| 2005/0076924 A1 | 4/2005 | Dobak, III | |
| 2005/0080374 A1 | 4/2005 | Esch et al. | |
| 2005/0096714 A1 | 5/2005 | Freedman et al. | |
| 2005/0107741 A1 | 5/2005 | Harrison et al. | |
| 2005/0120734 A1 | 6/2005 | Yon | |
| 2005/0274118 A1 | 12/2005 | McMurry et al. | |
| 2006/0064146 A1 | 3/2006 | Collins | |
| 2006/0136023 A1 | 6/2006 | Dobak, III | |
| 2006/0142827 A1 | 6/2006 | Willard et al. | |
| 2006/0161232 A1 | 7/2006 | Kasza et al. | |
| 2006/0167398 A1 | 7/2006 | Solar et al. | |
| 2006/0184231 A1 | 8/2006 | Rucker | |
| 2006/0293732 A1 | 12/2006 | Collins et al. | |
| 2007/0000278 A1 | 1/2007 | Collins et al. | |
| 2007/0005121 A1 | 1/2007 | Khanna | |
| 2007/0050002 A1 | 3/2007 | Elefteriades | |
| 2007/0191918 A1 | 8/2007 | MacHold et al. | |
| 2007/0244434 A1 | 10/2007 | Noda et al. | |
| 2007/0244531 A1 | 10/2007 | Noda et al. | |
| 2007/0293921 A1 | 12/2007 | Noda et al. | |
| 2008/0027383 A1 * | 1/2008 | Nahhas | 604/113 |
| 2008/0046046 A1 | 2/2008 | Ginsburg | |

| | | | |
|---|---|---|---|
| 2008/0114431 A1 | 5/2008 | Ginsburg | |
| 2008/0221651 A1 | 9/2008 | Dobak | |
| 2008/0271476 A1 | 11/2008 | Langguth | |
| 2008/0296190 A1 | 12/2008 | Marak et al. | |
| 2009/0265113 A1 | 10/2009 | Kimball | |
| 2010/0030190 A1 | 2/2010 | Singh | |
| 2010/0104493 A1 | 4/2010 | Hyde et al. | |
| 2010/0121159 A1 | 5/2010 | Burnett et al. | |
| 2010/0160705 A1 | 6/2010 | Kosters et al. | |
| 2010/0204765 A1 | 8/2010 | Hall et al. | |
| 2010/0324483 A1 | 12/2010 | Rozenberg et al. | |
| 2011/0029050 A1 | 2/2011 | Elefteriades et al. | |
| 2011/0066217 A1 | 3/2011 | Diller et al. | |
| 2011/0082423 A1* | 4/2011 | Joshi et al. | 604/113 |
| 2011/0125233 A1 | 5/2011 | Shen et al. | |
| 2011/0137248 A1 | 6/2011 | Winter | |
| 2011/0137249 A1 | 6/2011 | Collins et al. | |
| 2012/0095536 A1 | 4/2012 | Machold et al. | |
| 2012/0095537 A1 | 4/2012 | Hall et al. | |
| 2012/0116487 A1 | 5/2012 | Burnett et al. | |
| 2012/0123509 A1 | 5/2012 | Merrill et al. | |
| 2012/0172781 A1 | 7/2012 | Wang | |
| 2012/0221082 A1 | 8/2012 | Khanna | |
| 2013/0030411 A1 | 1/2013 | Kreck et al. | |
| 2013/0046232 A1 | 2/2013 | Walker et al. | |
| 2013/0046365 A1 | 2/2013 | Noda et al. | |
| 2013/0060311 A1 | 3/2013 | Noda et al. | |

FOREIGN PATENT DOCUMENTS

| | | |
|---|---|---|
| CN | 2538331 Y | 3/2003 |
| CN | 102309786 A | 1/2012 |
| EP | 1028679 B1 | 8/2000 |
| EP | 1049412 A1 | 11/2000 |
| EP | 1205167 A2 | 5/2002 |
| EP | 1406566 B1 | 4/2004 |
| EP | 2514453 A1 | 10/2012 |
| IT | 1245824 B | 5/1992 |
| JP | 2008154751 A | 7/2008 |
| JP | 04610825 B2 | 1/2011 |
| WO | 0009054 A1 | 2/2000 |
| WO | 0010494 A1 | 3/2000 |
| WO | 0047145 A1 | 8/2000 |
| WO | 0053135 A1 | 9/2000 |
| WO | 0057823 A1 | 10/2000 |
| WO | 0059419 A1 | 10/2000 |
| WO | 0062837 A2 | 10/2000 |
| WO | 0110323 A1 | 2/2001 |
| WO | 0110365 A1 | 2/2001 |
| WO | 0112061 A1 | 2/2001 |
| WO | 0126590 A1 | 4/2001 |
| WO | 0136035 A1 | 5/2001 |
| WO | 0141708 A2 | 6/2001 |
| WO | 0143661 A2 | 6/2001 |
| WO | 0149236 A2 | 7/2001 |
| WO | 0152781 A1 | 7/2001 |
| WO | 0156517 A1 | 8/2001 |
| WO | 0158397 A1 | 8/2001 |
| WO | 0166052 A1 | 9/2001 |
| WO | 0174276 A1 | 10/2001 |
| WO | 0195840 A1 | 12/2001 |
| WO | 0226176 A1 | 4/2002 |
| WO | 0226285 A2 | 4/2002 |
| WO | 0228458 A1 | 4/2002 |
| WO | 0236180 A2 | 5/2002 |
| WO | 0238091 A1 | 5/2002 |
| WO | 02058606 A1 | 8/2002 |
| WO | 02068928 A2 | 9/2002 |
| WO | 03015672 A1 | 2/2003 |
| WO | 03015673 A1 | 2/2003 |
| WO | 03028796 A1 | 4/2003 |
| WO | 03037158 A2 | 5/2003 |
| WO | 03066137 A1 | 8/2003 |
| WO | 2004023982 A2 | 5/2004 |
| WO | 2004075949 A2 | 9/2004 |
| WO | 2005112843 A1 | 12/2005 |
| WO | 2007002946 A2 | 1/2007 |
| WO | 2007005026 A2 | 1/2007 |
| WO | 2007078463 A1 | 7/2007 |
| WO | 2009023797 A1 | 2/2009 |
| WO | 2009094601 A1 | 7/2009 |
| WO | 2009102803 A2 | 8/2009 |
| WO | 2009124552 A2 | 10/2009 |
| WO | 2009124553 A2 | 10/2009 |
| WO | 2010111778 A1 | 10/2010 |
| WO | 2011103208 A2 | 8/2011 |
| WO | 2011156565 A1 | 12/2011 |
| WO | 2012006184 A2 | 1/2012 |
| WO | 2012012740 A1 | 1/2012 |
| WO | 2013049637 A1 | 4/2013 |

OTHER PUBLICATIONS

Bernard, S.A., Gray, T.W., Buist, M.D., Jones, B.M., Silvester, W., Guthridge, G., et al. (2002), Treatment of comatose survivors of out-of-hospital cardiac arrest with induced hypothermia. The New England Journal of Medicine, 346(8), 557-563.

Keller, E. Imhof, Ho G., Gasser, S., Terzic, A., & Yonekawa, Y. (2003). Endovascular cooling with heat exchange catheters: A new method to induce and maintain hypothermia. Intensive Care Medicine, 29(6), 939-943.

Nolan, J.P., Morley, P.T., Hock, T.L., Hicking, R.W., & Advancement Life Support Task Force of the International Liaison Committee on Resuscitation. (2003). Therapeutic hypothermia after cardiac arrest. An advisory statement by the advancement life support task force of the international liaison committee on resuscitation. Resuscitation, 57(3), 231-235.

Al-Senani, F.M., Grattagnino, C., Grotta, J.C., Saiki, R., Wood, D., Chung, W., et al. (2004). A prospective, multicenter pilot study to evaluate the feasibility and safety of using the CoolGard(tm) system and Icy(tm) catheter following cardiac arrest. Resuscitation, 62(2), 143-150.

Diringer, M.N., & Neurocritical Care Fever Reduction Trial Group (2004). Treatment of fever in the neurologic intensive care unit with a catheter-based heat exchange system, Critical Care Medicine, 32(2), 559-564.

Huppman, S., Johnson, J. Kang, S. & Wacker, E.; Intravenous Cooling System to Induce Mild Hypothermia; University of Pittsburgh Senior Design, BioE 1160-1161; Apr. 10, 2007, 27 pages.

Huppman, S., Johnson, J. Kang, S. & Wacker, E.; IV Cooling System for Hypothermia; SBIR Proposal; Apr. 17, 2007; 22 pages.

* cited by examiner

RAPID FLUID COOLING DEVICES AND METHODS FOR COOLING FLUIDS

CROSS REFERENCE TO RELATED APPLICATIONS

This divisional patent application claims the benefit of U.S. patent application Ser. No. 12/711,749, filed Feb. 24, 2010, and titled "RAPID FLUID COOLING DEVICES AND METHODS FOR COOLING FLUIDS," which claims the benefit of U.S. Provisional Patent Application Ser. No. 61/154,972, filed Feb. 24, 2009, titled "RAPID FLUID COOLING DEVICES AND METHODS FOR COOLING FLUIDS;" the contents of which are incorporated by reference herein in their entireties.

TECHNICAL FIELD

The present invention relates generally to fluid cooling devices. More particularly, the present invention relates to the cooling of fluids by endothermic reaction.

BACKGROUND

The cooling of core body temperature, such as for inducing hypothermia, is a medical treatment increasingly being used to treat patients as part of various medical-related procedures. Administering cooled intravenous fluids to induce hypothermia in cardiac arrest patients in the pre-hospital setting has been found to improve the likelihood of those patients being subsequently discharged from the hospital neurologically intact. Induced hypothermia therapy has proven effective in postponing damage to tissues caused by insufficient blood flow and oxygen deprivation. The smaller the time difference between cardiac arrest and induced hypothermia, the higher the likelihood of successful treatment. While there are in-hospital products available for inducing hypothermia, these products are not feasible for use in the pre-hospital setting.

The cooling of intravenous fluids for use in the pre-hospital setting is currently achieved though the use of conventional, bulky refrigeration units or simply ice-filled containers. Primary responders are typically unable to carry both conventional refrigerators and cardiac arrest patients simultaneously on-board a vehicle (e.g., ambulance, helicopter, etc.), or at least it is impractical to do so, for various reasons such as the space required for the refrigeration unit or ice-filled container and the fact that induced hypothermia as a treatment will be indicated in only a small fraction of the emergency situations encountered. Consequently, a second emergency vehicle carrying a refrigeration unit is required to intercept the primary responder and supply the primary responder with cooled intravenous fluids to administer to the patient. Once the cooled fluids are taken out of the refrigerator or ice-filled container, the fluids immediately begin to warm and there is currently no method available to effectively stop the warming process.

In recent years, there has been evidence supporting the use of induced hypothermia therapy in various other medical applications, including cardiac surgery and stroke recovery. As more medical discoveries are made, the potential uses of cooled fluids are likely to increase in both the pre-hospital and in-hospital settings.

In view of the foregoing, there is an ongoing need for cost-effective, efficient, portable, and compact fluid cooling devices for use in the medical field in general, and for use in rapidly cooling intravenous fluids in particular such as for inducing hypothermia in patients requiring medical attention, as well as for use in various non-medical fields.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one implementation, a cooling device includes a target fluid inlet, a target fluid outlet, an inner conduit, and a chamber surrounding the inner conduit. The inner conduit fluidly communicates with the target fluid inlet and the target fluid outlet, and provides a flow path for a target fluid to be cooled. The chamber surrounding the inner conduit contains a first endothermic reactant and includes a reactant inlet selectively alterable from a closed state to an open state. When the reactant inlet is in the closed state, the first endothermic reactant is isolated from a second endothermic reactant and no endothermic reaction occurs. When the reactant inlet is in the open state, the reactant inlet provides a flow path for enabling the second endothermic reactant to come into contact with the first endothermic reactant in the chamber for initiating the endothermic reaction and cooling the target fluid in the inner conduit.

According to another implementation, the reactant inlet of the cooling device may further include a barrier. When the reactant inlet is in the closed state, the barrier may divide the chamber into a first region containing the first endothermic reactant, and a second region containing the second endothermic reactant. The cooling device may include an actuator configured to open the barrier wherein the reactant inlet is altered to the open state.

According to another implementation, the cooling device includes a pressure release valve adapted to communicate with the chamber, wherein the pressure release valve allows flow from the chamber to a receptacle adapted to communicate with the pressure release valve when the pressure in the chamber increases to a predetermined critical pressure.

According to another implementation, at least a portion of the chamber is flexible such that the volume of the chamber is expandable.

According to another implementation, the cooling device includes an insulating material surrounding the chamber.

According to another implementation, the target fluid includes saline solution. In another implementation, the target fluid further includes a therapeutically active drug.

According to another implementation, the reactant inlet comprises a fitting configured for connection to an external source of the second endothermic reactant. In another implementation, the reactant inlet comprises a valve.

According to another implementation, an intravenous target fluid delivery system includes an IV target fluid reservoir, a cooling device, and a cooled IV target fluid receiving tube. The IV target fluid reservoir contains an IV target fluid to be cooled in the cooling device. The IV target fluid reservoir fluidly communicates with a target fluid inlet of the cooling device. The cooled IV target fluid receiving tube fluidly communicates with a target fluid outlet of the cooling device, and is configured for intravenously administering the cooled IV target fluid to a patient.

According to another implementation, the first endothermic reactant includes an inorganic salt such as, for example, ammonium nitrate, ammonium chloride, potassium chloride, etc. The second endothermic reactant may, for example, include water.

According to another implementation, the reactant inlet includes a barrier and in the closed state, the barrier divides the chamber into a first region containing the first endothermic reactant, and a second region containing the second endothermic reactant. In some implementations, an actuator is configured to open the barrier wherein the reactant inlet is altered to an open state. The actuator may be configured to puncture the barrier. Alternatively, the actuator may be configured to move at least a portion of the barrier to create an opening therethrough.

In some implementations, the IV target fluid reservoir may include an IV bag. The cooled IV target fluid receiving tube may include an IV catheter.

According to another implementation, a method is provided for cooling a target fluid. In the method, a target fluid is flowed from a target fluid inlet of a cooling device, through the cooling device, and to a target fluid outlet of the cooling device. While flowing the target fluid, heat is removed from the target fluid by conducting an endothermic reaction in the cooling device.

According to another implementation, a method is provided for treating a patient. A target fluid to be cooled is flowed from a reservoir through a target fluid inlet of a cooling device, and into an inner conduit of the cooling device. The cooling device includes a chamber surrounding the inner conduit and containing a first endothermic reactant. The chamber includes a reactant inlet selectively alterable from a closed state to an open state, wherein in the closed state, the first endothermic reactant is isolated from a second endothermic reactant and no endothermic reaction occurs. The endothermic reaction is initiated and the target fluid in the inner conduit is cooled by altering the reactant inlet from the closed state to the open state, wherein the reactant inlet provides a flow path for enabling the second endothermic reactant to come into contact with the first endothermic reactant in the chamber. The cooled target fluid is flowed through a target fluid outlet of the cooling device into a cooled-fluid-receiving tube. The cooled target fluid is administered to the patient intravenously to reduce the patient's core body temperature.

In some implementations, the target fluid includes saline solution. In further implementations, the target fluid further comprises a therapeutically active drug.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

By way of example, FIGS. 1-7 illustrate various implementations of a fluid cooling device, a method for cooling a target fluid, a method for treating a patient, and a related system. The various implementations provide a highly effective, compact, transportable, and efficient solution for rapidly cooling a target fluid for use, as for example, in the pre-hospital setting for intravenously inducing hypothermia or otherwise significantly reducing the core body temperature in cardiac arrest patients as well as for other medical uses and non-medical uses. As noted above, the less the difference in time between cardiac arrest and induced hypothermia, the higher the likelihood of success in subsequently discharging cardiac arrest patients from the hospital neurologically intact. Hypothermia is defined as a body temperature significantly below 37° C., and there are various levels of hypothermia. For example, mild hypothermia is defined as a body temperature of about 34° C., moderate hypothermia is defined as a body temperature of about 23-32° C. and profound hypothermia is defined as a body temperature of about 12-20° C. See Stedman's Medical Dictionary, 26$^{th}$ Edition, 1995. A fluid cooling device consistent with the present teachings has experimentally demonstrated superior performance in providing a cooled target fluid for use in the pre-hospital setting, as compared with the current method of cooling fluids in the pre-hospital setting via conventional refrigeration. For example, a fluid cooling device according to the present teachings has experimentally cooled a target fluid (i.e., saline solution) from room temperature to about 4° C. in about 1.5 to 2.0 minutes, wherein ammonium nitrate and water were utilized as the endothermic reactants in the cooling device. The cooling device according to the present teachings may be sized and configured for compatibility with associated fluid delivery components. For example, the cooling device may be easily connected to standardized intravenous delivery equipment to function as an in-line, on-demand chilling device. All or part of the cooling device may be sterilizable and reusable, or alternatively may be configured as a disposable single-use device.

Figure 1:
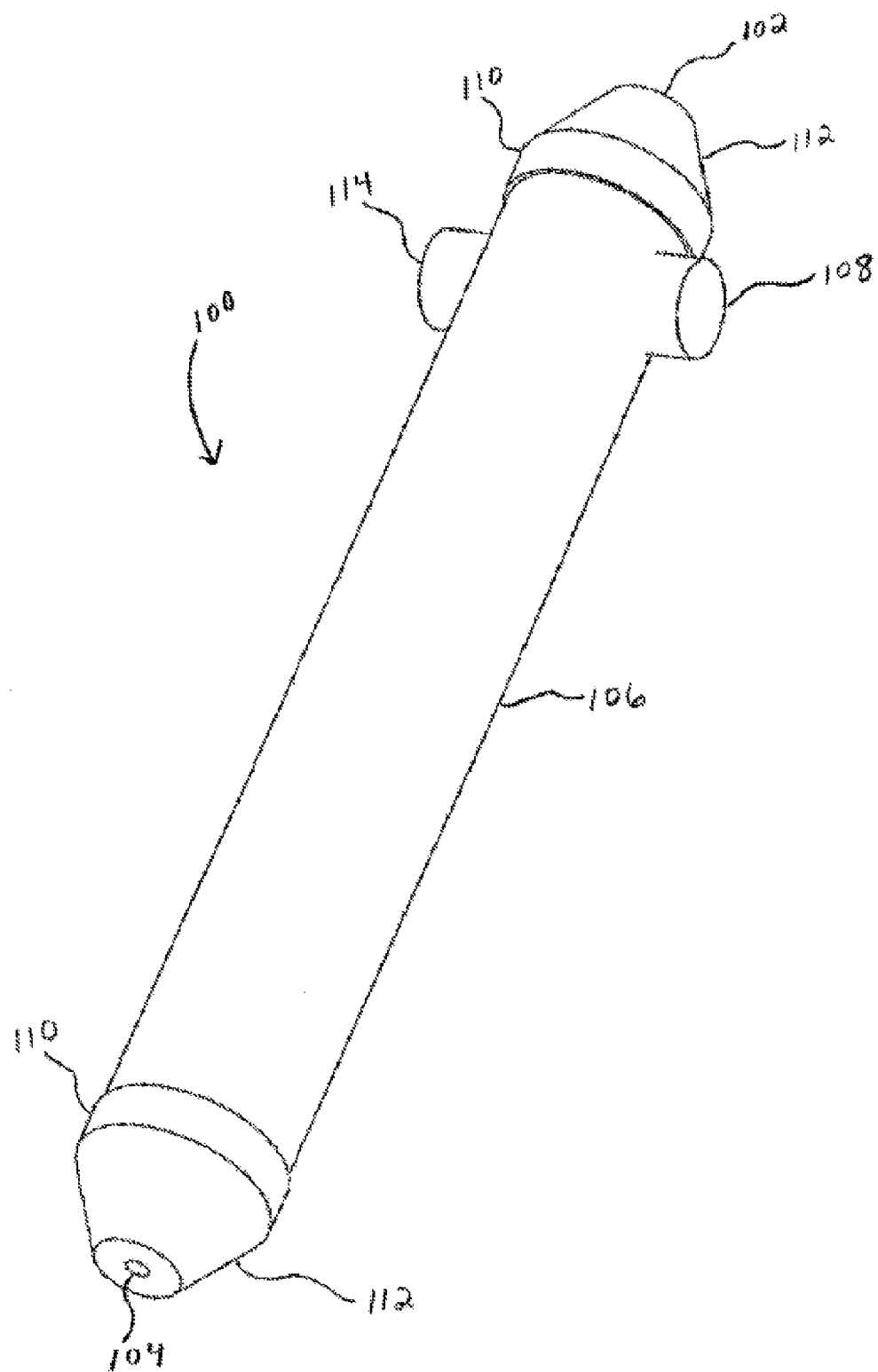
FIG. 1 is a simplified perspective view of an example of a fluid cooling device according to the present teachings.

FIG. 1 is a simplified perspective view of an example of a fluid cooling device 100 according to the present teachings. The cooling device 100 generally includes a target fluid inlet 102 through which a target fluid (e.g., saline solution) to be cooled may enter the cooling device 100, and a target fluid outlet 104 through which the target fluid may exit the cooling device 100. The cooling device 100 also generally includes a chamber 106 surrounding one or more inner conduits (not shown in FIG. 1) between the target fluid inlet 102 and the target fluid outlet 104, and containing a first endothermic reactant (e.g., ammonium nitrate, ammonium chloride, potassium chloride, or the like). The first endothermic reactant may, for example, be packed into the chamber 106 in any suitable form such as powder, pellets, grains, gel, colloid, suspension, liquid, or the like, and may fill the volume in the chamber 106 around the inner conduit or conduits. The inner conduit fluidly communicates with the target fluid inlet 102 and the target fluid outlet 104, and provides one or more flow paths for a target fluid to be cooled. An example of an inner conduit provided as one or more inner helical conduits is described below with respect to FIGS. 2 and 3. Those skilled in the art will appreciate that the inner conduit(s) may be constructed of various materials (e.g., medical grade metals, thermally conductive plastics, and the like) and may include various shapes and cross-sectional areas so as to optimize the available surface area for heat transfer. The target fluid inlet 102 may generally be configured to accommodate the size of any inlet tubing or fitting connected to the target fluid inlet 102. The target fluid outlet 104 may generally be configured to accommodate the size of any outlet tubing or fitting connected to the target fluid outlet 104. The chamber 106 also generally includes a reactant inlet 108 that is selectively alterable from a closed state to an open state. The reactant inlet 108 may include, for example, a Luer-Lock™ port or any valve or fitting switchable between closed and open states, or an openable or frangible barrier. In the closed state, the first endothermic reactant is isolated from a second endothermic reactant and no endothermic reaction occurs. In the open state, the reactant inlet 108 provides a flow path for enabling the second endothermic reactant to come into contact with the first endothermic reactant in the chamber 106 for initiating the endothermic reaction and consequently cooling the target fluid in the inner conduit. As in the case of the first endothermic reactant, the second endothermic reactant may be provided in any suitable form (e.g., solid, semi-solid, colloidal, liquid, etc.). Moreover, the first and/or second endothermic reactant may include any suitable additive that promotes or optimizes the endothermic reaction.

As appreciated by persons skilled in the art, various types of endothermic reactions exist and thus the specific reactants utilized in the cooling device 100 will depend on the particular endothermic reaction being implemented. As examples, ammonium nitrate, ammonium chloride, or potassium chloride may be utilized as the first endothermic reactant, and in each case, water may be utilized as the flowable second endothermic reactant. Other flowable materials may also be suitable for serving as the second endothermic reactant. Generally, the cooling device 100 may employ any combination of reactants that, when combined, result in an endothermic reaction suitable for rapid cooling of a selected target fluid such as, for example, saline solution. The second endothermic reactant may be flowed into the chamber 106 via the reactant inlet 108 by any suitable means such as, for example, utilizing a syringe (not shown) or other external source of reactant. Alternatively, the second endothermic reactant may be provided internally within the cooling device as described by example below in conjunction with FIG. 4. Those skilled in the art will appreciate that in some implementations, the first endothermic reactant may not be pre-loaded in the chamber 106. For example, both the first and second endothermic reactants may be supplied from external sources (e.g., syringes) into the chamber 106 via the reactant inlet 108 in any order (or from two separate reactant inlets) for initiating the endothermic reaction. Having the first endothermic reactant and/or the second endothermic reactant preloaded in the chamber 106 may be particularly useful in implementations in which the cooling device 100 is utilized to rapidly cool intravenous fluids in the pre-hospital setting, for example.

In the present example, the chamber 106 may be constructed of, for example, PVC plastic. At each end of the chamber 106, an end plate 110 may be attached to the chamber 106 by any suitable means, and may be constructed to accommodate the ends of the inner conduits. An end cap 112 may also be secured by any suitable means to the end plate 110 and/or chamber 106 at each end of the chamber 106. The end caps 112 may be tapered or otherwise configured to accommodate the positions of the inner conduit(s) and/or the flow transitions between the inner conduit(s) of the chamber 106 and the target fluid inlet 102 and target fluid outlet 104. Both the end plates 110 and the end caps 112 may be constructed of, for example, ABS plastic. In some implementations, a pressure release valve 114 may optionally be provided to communicate with the chamber 106 such that pressure may release from the chamber 106 to, for example, a receptacle (not shown) adapted to communicate with the pressure release valve 114 when the pressure in the chamber 106 increases to a predetermined critical pressure. For example, if a syringe is used to admit the second endothermic reactant into the chamber 106 via the reactant inlet 108, the pressure release valve 114 may be used to release any excess pressure in the chamber 106 resulting from utilization of the syringe. The use of a receptacle at the pressure release valve 114 maintains the cooling device 100 as a closed system and ensures that the endothermic reactants remain isolated from the environment. Alternatively, element 114 may represent a fluid connection to a flexible chamber that allows for expansion. As a further alternative, at least a portion of the chamber 106 may be flexible to allow for expansion. The chamber 106 may also be surrounded by an insulating material (e.g., polypropylene foam covered in vinyl fabric) to ensure a minimum amount of heat transfer into the cooling device 100 from the outside environment.

The cooling device 100 in FIG. 1 may be used to rapidly, effectively and reliably supply cooled fluids in a manner which does not require the aid of any other device. In one specific yet non-limiting example, the cooling device 100 may be utilized to quickly supply cooled saline solution for intravenous administration to cardiac arrest patients in the pre-hospital setting, so as to reduce the core body temperature of the patients. The cooling device 100 is completely isolated from the external environment, ensuring no contamination of the target liquid, any potential user, and any potential patient while the cooling device 100 is in use. The cooling device 100 may also be utilized in various other settings, e.g., stroke therapy and cardiac surgery. More generally, the cooling device 100 may be utilized in a wide variety of non-medical as well as medical applications for cooling various liquids, gases, vapors, suspensions, etc. The cooling device 100 may be portable, easily storable and easily disposed of after use. The cooling device 100 may be easily connected to input tubing and output tubing for use as an in-line device, as described in further detail below with respect to FIG. 7. The cooling device 100 according to the present teachings may be manufactured in varying sizes and dimensions so as to allow for various temperatures of the target fluid at the target fluid outlet 104 of the cooling device 100. For example, reducing the length of the cooling device 100 may result in a higher temperature of the target fluid at the target fluid outlet 104 as a result of a decrease in surface area utilized for heat transfer. As another example, the cooling device 100 according to the present teachings may be manufactured with varying amounts of the first endothermic reactant so as to allow for various temperatures of the target fluid at the target fluid outlet 104 of the cooling device 100. As yet another example, different cooling devices 100 according to the present teachings may be manufactured with different endothermic reactants so as to allow for various temperatures of the target fluid at the target fluid outlet 104 of the cooling devices 100. In some implementations a target fluid flowing through the cooling device 100 may be cooled from room temperature down to about 3 or 4° C. upon exit from the cooling device 100. The time required for this amount of cooling to occur from the target fluid inlet 102 to the target fluid outlet 104 will depend on a variety of factors, including for example the volume of the chamber 106 and of the reactant loaded therein, the internal diameter and length of the inner conduit(s) and thus the resulting flow rate and residence time of the target fluid in the chamber 106, as well as the specific endothermic reactants utilized.

Figure 2:
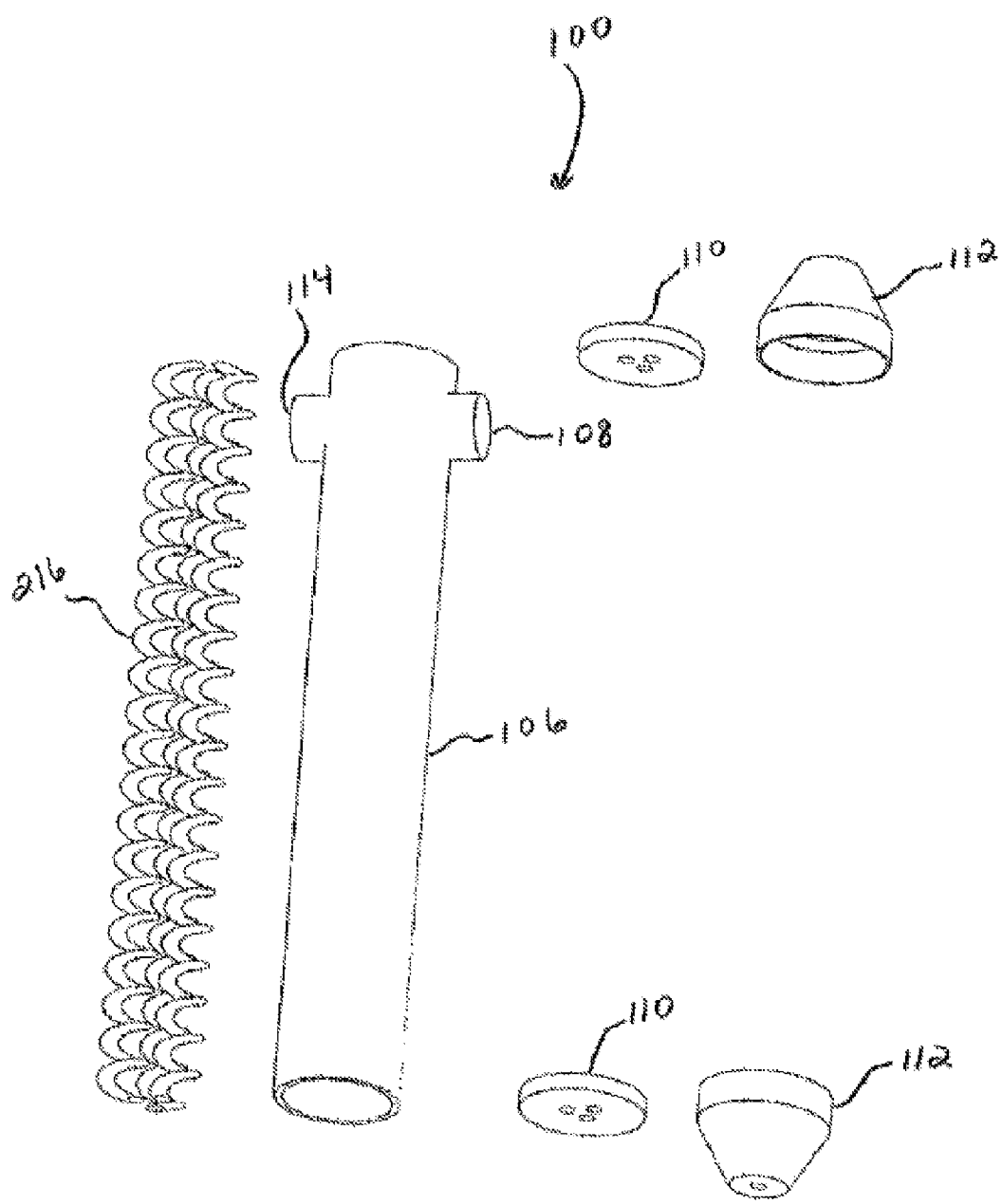
FIG. 2 is an exploded perspective view of an example of a fluid cooling device according to the present teachings.
Figure 3:
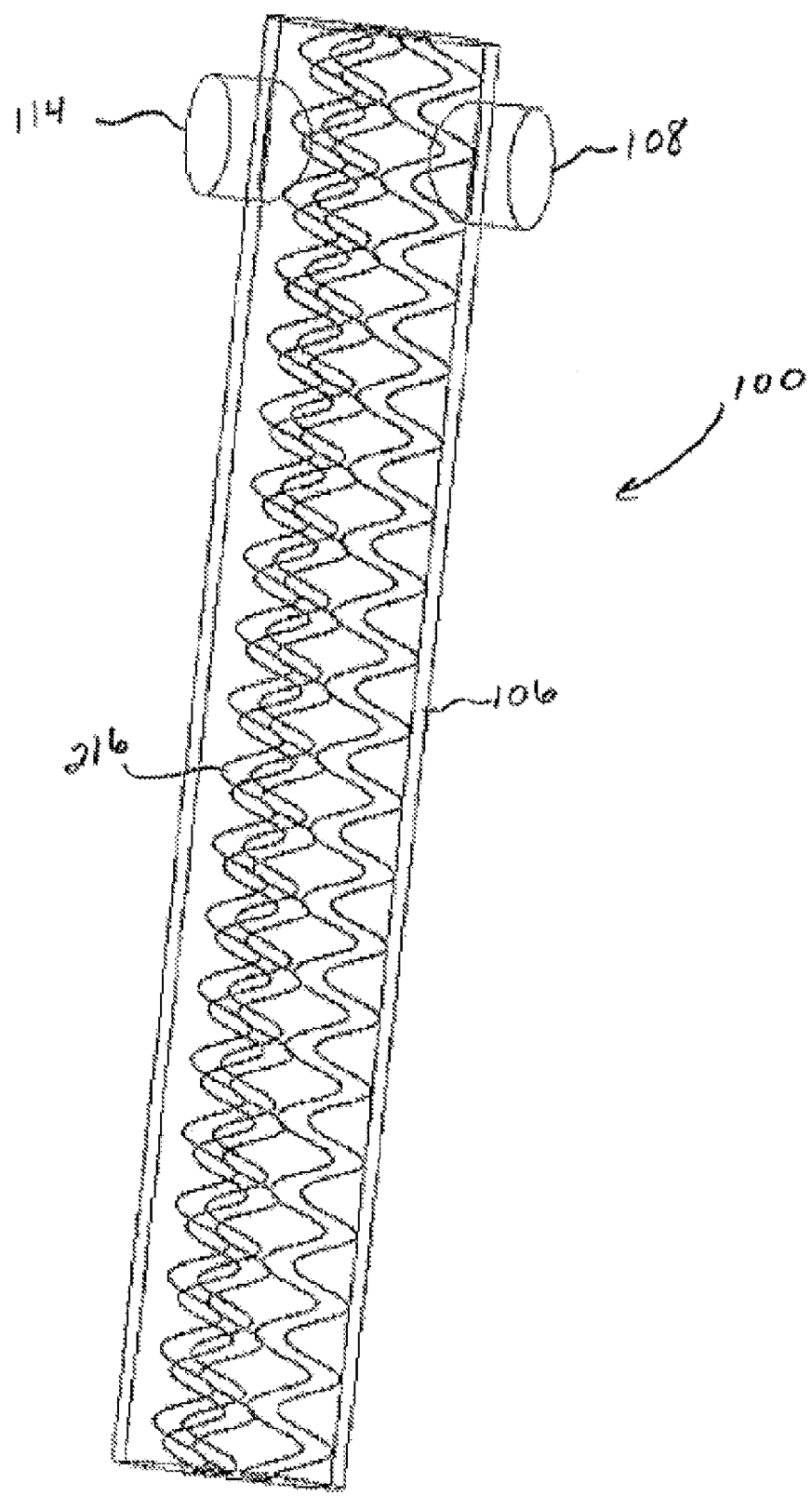
FIG. 3 is a cut-away view of a portion of a chamber surrounding inner helical conduits according to the present teachings.

FIG. 2 is an exploded perspective view of an example of the fluid cooling device 100 discussed above. The fluid cooling device 100 may be utilized as described above with respect to FIG. 1, or as otherwise described in the present teachings. The cooling device 100 also includes the chamber 106 containing the first endothermic reactant. As an example, during assembly the first endothermic reactant may be loaded through one of the initially open ends of the chamber 106. The cooling device 100 may also include an inner conduit 216 through which the target fluid flows from the target fluid inlet 102 to the target fluid outlet 104 in thermal communication with, but fluidly isolated from, the endothermic reactants present in the chamber 106. The inner conduit 216 may be configured to increase the surface area available for heat transfer. Thus, in the present example, the inner conduit 216 may include one or more inner helical conduits 216. When the cooling device 100 is assembled, the inner helical conduits 216 fluidly communicate with the target fluid inlet 102 and the target fluid outlet 104, and provide flow paths for the target fluid to be cooled. When the cooling device 100 is assembled, the chamber 106 surrounds the inner helical conduits 216 as illustrated in FIG. 3. As an alternative to the illustrated helical configuration, the inner conduits 216 may have any other suitable configuration, shape or profile that increases their lengths, increases their outer surface areas, and/or maximizes their thermal contact with the endothermic reactants.

In the present example, the inner helical conduits 216 may be constructed of a thermally conductive material providing adequate heat transfer such as, for example, various metals, e.g., stainless steel, titanium, aluminum, or brass, and certain thermally conductive plastics. In some implementations, the inner helical conduits 216 may be constructed of medical grade conductive materials to ensure against contamination of the target fluid for medical uses. If needed, the inside and/or outside surfaces of the inner helical conduits 216 may be coated with biocompatible or protective barrier films, as appreciated by persons skilled in the art. When the cooling device 100 is assembled, an end plate 110 may be attached to the chamber 106 at each end of the chamber 106, and may be constructed to accommodate the ends of the inner helical conduits 216 and support the inner helical conduits 216 in the chamber 106 in a fixed manner. For instance, in the present example in which three inner helical conduits 216 are utilized, each end plate 110 may include three through-bores respectively communicating with the three inner helical conduits 216 to facilitate flow-splitting from the target fluid inlet 102 and flow-merging to the target fluid outlet 104. An end cap 112 may also be secured by any suitable means (e.g., through the use of an adhesive) to the outside of the end plate 110 and/or the chamber 106 at each end of the chamber 106 when the cooling device 100 is assembled. As also noted above, the chamber 106 may also be surrounded by an insulating material (not specifically shown) to ensure a minimum amount of heat transfer into the cooling device 100 from the outside environment.

FIG. 3 is a cut-away view of a portion of the fluid cooling device 100. Specifically, FIG. 3 illustrates the three inner helical conduits 216 of the present example after installation in the surrounding chamber 106. In this example, the total amount of heat removed from the target fluid as it flows from the inlet side to the outlet side of the chamber 106, and the rate of heat removal, are increased by splitting the flow into more than one inner conduit 216 and by coiling the inner conduits 216 so as to increase their lengths from inlet to outlet. The coiled or helical shapes are but one example; other examples include serpentine shapes and various other multi-turn configurations. As another example, the inner conduits 216 may be provided with cooling fins. Generally, no limitation is placed on the internal diameter(s) of the inner conduit(s) 216, so long as target fluid flow therethrough is unimpeded and travel time is sufficient to ensure a desired amount of heat rejection to the surrounding chamber 106. It can also be seen in FIG. 3 that an ample volume is provided around and between the inner conduits 216 for filling the chamber 106 with the selected endothermic reactants. Upon initiation of the endothermic reaction in the chamber 106, thermal gradients are established from the inner conduits 216 and outward in a multitude of directions.

Figure 4:
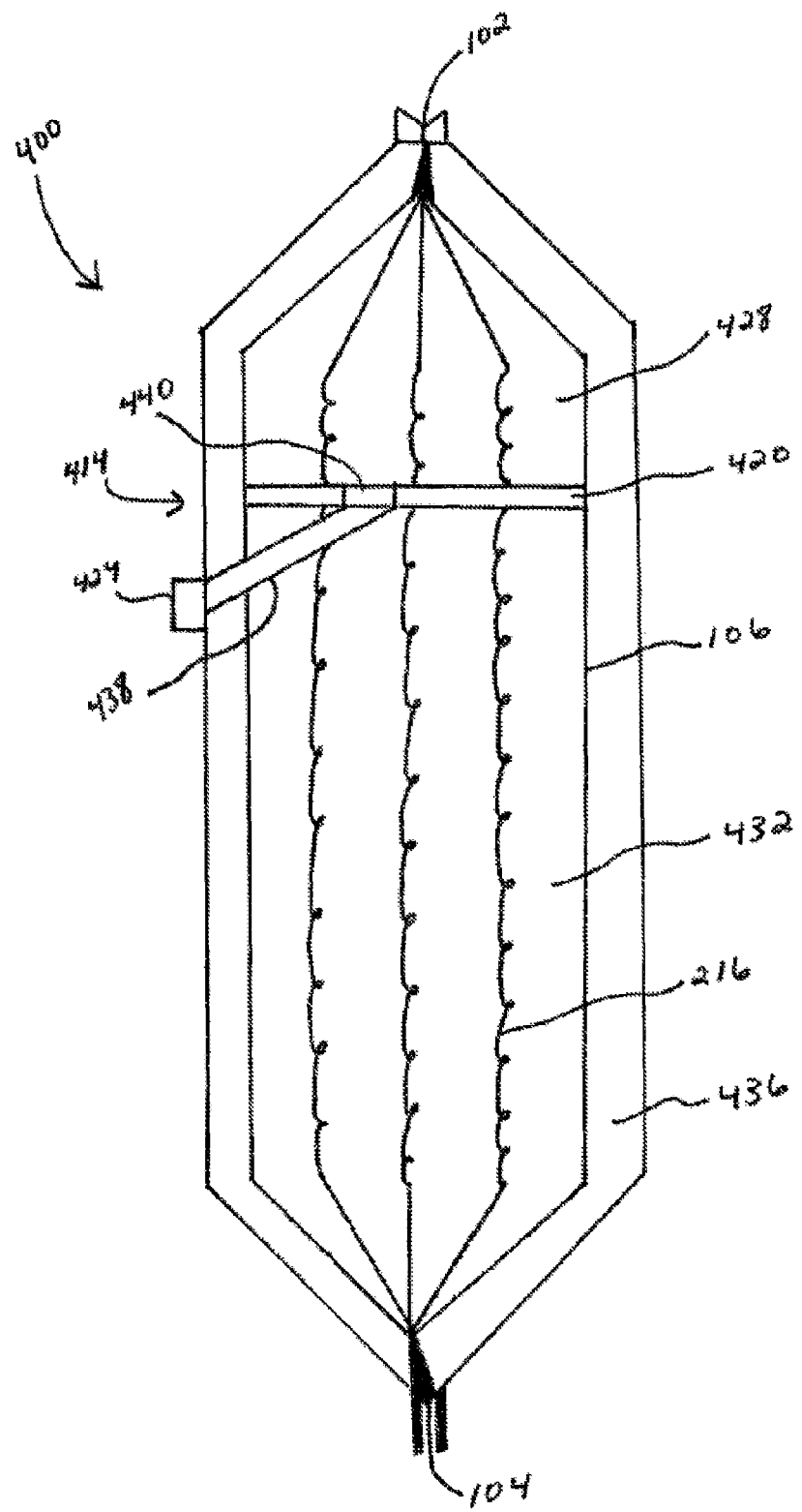
FIG. 4 is a cross-sectional elevation view of another example of a fluid cooling device according to the present teachings that illustrates a barrier within the chamber.

FIG. 4 is a cross-sectional elevation view of another example of a fluid cooling device 400 according to the present teachings. As in the previous example, the cooling device 400 includes a target fluid inlet 102 and a target fluid outlet 104, which in this example include female and male Luer-type fittings, respectively. The cooling device 400 also includes inner helical conduits 216 fluidly communicating with the target fluid inlet 102 and the target fluid outlet 104 and providing flow paths for the target fluid to be cooled. The cooling device 400 includes a chamber 106 surrounding the inner helical conduits 216 and containing a first endothermic reactant. FIG. 4 also illustrates an insulation layer 436 surrounding the chamber 106 which may be included in the cooling device 400, as described above. The chamber 106 further includes a reactant inlet 414 selectively alterable from a closed state to an open state. In this example, the reactant inlet 414 includes a frangible or openable barrier 420 spanning the internal cross-section of the chamber 106. In the closed state, the barrier 420 may divide the chamber 106 into a first region 432 containing the first endothermic reactant (e.g., ammonium nitrate) and a second region 428 containing the second endothermic reactant (e.g., water). In the closed state, the first endothermic reactant is isolated from the second endothermic reactant by the barrier 420 and thus no endothermic reaction occurs. When the reactant inlet 414 is altered to the open state, such as by breaking, puncturing or otherwise opening the barrier 420, an opening 440 is created to provide a flow path for enabling the second endothermic reactant to come into contact with the first endothermic reactant for initiating the endothermic reaction and cooling the target fluid in the inner helical conduits 216. Alternatively, the first endothermic reactant may flow from the first region 432 into the second region 428 and thus into contact with the second endothermic reactant. More generally, at least one of the reactants is flowable so that interaction among the reactants occurs after the opening 440 in the barrier 420 has been formed.

In the present example, the barrier 420 may be opened by any suitable user-actuated opening mechanism 424. For example, the mechanism 424 may include a button or knob that, when actuated by the user (e.g., pressed, pulled, slid, rotated, etc.), actuates a puncturing device 438 that breaks the barrier 420 and hence alters the reactant inlet 414 to the open state by creating the opening 440, which allows the first and second endothermic reactants to mix or combine within the chamber 106. As used herein, terms such as "mix" and "combine" encompass any type of contact or interaction between reactants that results in the endothermic reaction utilized as the cooling mechanism according to the present teachings. The exact mechanics of the interaction between the endothermic reactants and the particular reaction kinetics will depend on the type of endothermic reaction conducted in a given implementation, one non-limiting example being the dissolution of certain nitrates or chlorides in a suitable solvent such as water as noted above. As another example, the mechanism 424 may include or operate as a switch that, when actuated by the user, moves the barrier 420 or a portion thereof (e.g., a valve, shutter, or sliding mechanism) to an open state, thereby creating the opening 440 and allowing the second endothermic reactant to flow. In this latter case, the element 438 may represent any suitable mechanical linkage between the mechanism 424 and the barrier 420. For instance, the mechanism 424 may be linked to the barrier 420 such that pushing or pulling the mechanism 424 translates or rotates all or part of the barrier 420 to create the opening 440. As another alternative, the mechanism 424 may be configured such that sliding the mechanism 424 a short distance causes the barrier 420 to open in the manner of a shutter. In all of the foregoing alternatives, the term "breaking" as used in conjunction with altering the barrier 420 encompasses any means by which the opening 440 may be created (e.g., puncturing, moving the barrier 420 or a portion thereof, etc.), and thus in this context terms such as "breaking" and "opening" are used interchangeably. Moreover, in conjunction with breaking or opening the barrier 420, the cooling device 400 may be shaken or agitated by the user to promote the mixing of the reactants.

Figure 5:
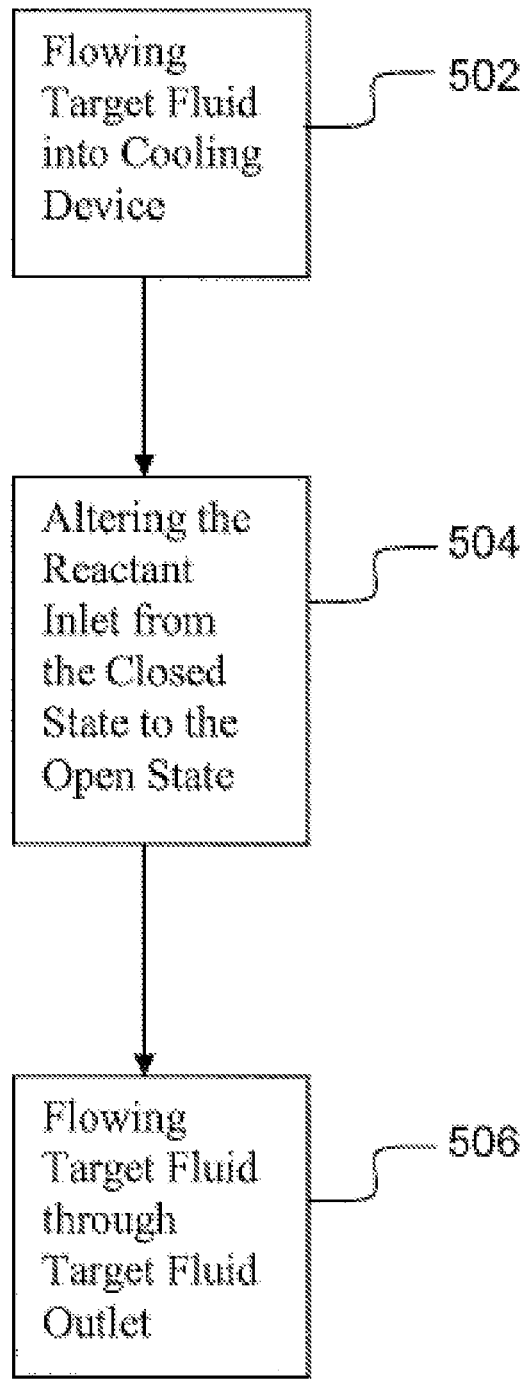
FIG. 5 is a flow diagram illustrating a method for cooling a target fluid according to the present teachings.

FIG. 5 is a flow diagram illustrating an example of a method for cooling a target fluid according to the present teachings. The method may be implemented by utilizing a cooling device 100 or 400 such as described above and illustrated in FIGS. 1-4. The first step 502 in the method generally includes flowing the target fluid through a target fluid inlet into an inner conduit or conduits of a cooling device. The target fluid may include, for example, saline solution or any other fluid desired to be cooled in a particular application. The cooling device of the present example may include a chamber surrounding the inner conduit and containing a first endothermic reactant (e.g., ammonium nitrate). The chamber may include a reactant inlet that is selectively alterable from a closed state to an open state. The reactant inlet may be internal or external to the chamber as described above. When the reactant inlet is in the closed state, the first endothermic reactant is isolated from a second endothermic reactant and no endothermic reaction occurs. The second step 504 in the present example includes altering the reactant inlet from the closed state to the open state. Consequently, the reactant inlet provides a flow path for enabling the second endothermic reactant (e.g., water) to come into contact with the first endothermic reactant in the chamber for initiating the endothermic reaction and cooling the target fluid in the inner conduit. The target fluid may be cooled to a temperature of, for example, 3 to 4 degrees Celsius, or a variety of other temperatures, depending on the particular application of the method. In some implementations, the second step 504 may be performed prior to carrying out the first step 504, so as to allow the reaction to begin before flowing the target fluid through the target fluid inlet. The third step 506 in the present example includes flowing the target fluid through a target fluid outlet of the cooling device to a selected destination for the cooled target fluid such as into a receiving tube. In one example of one implementation of the present teachings, the cooled-fluid-receiving tube may include IV tubing for use in the medical field.

Figure 6:
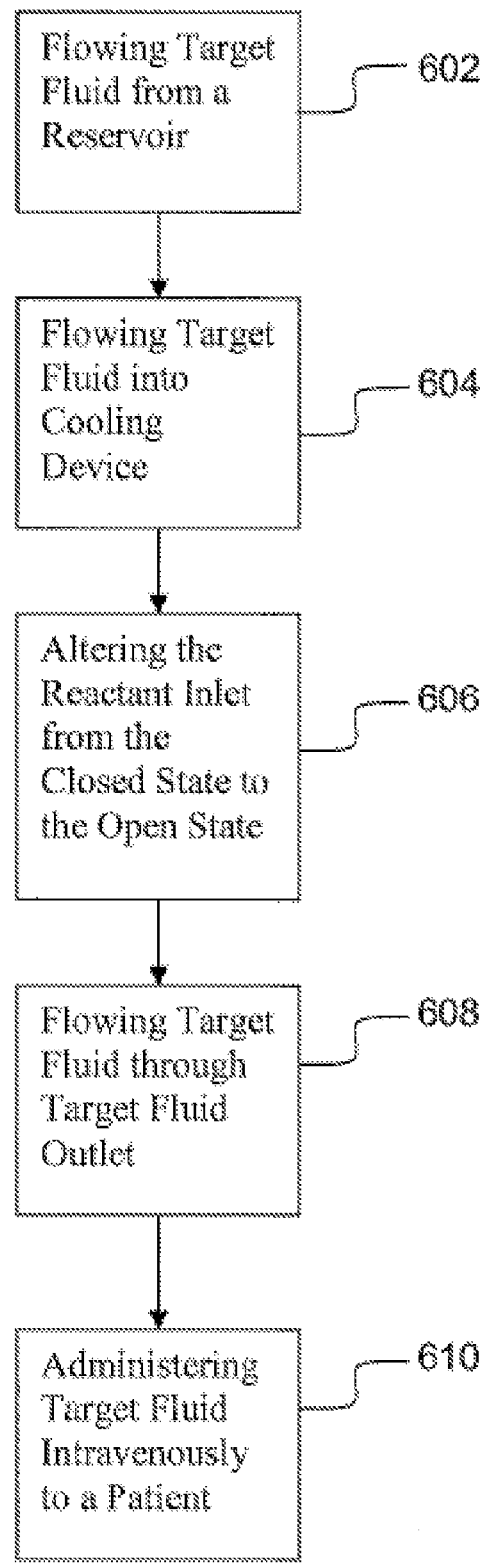
FIG. 6 is a flow diagram illustrating a method for treating a patient according to the present teachings.

FIG. 6 is a flow diagram illustrating an example of a method for treating a patient according to the present teachings. The present method may be used, for example, in the treatment of cardiac arrest patients in the pre-hospital or in-hospital settings. The present method may also be used, as another example, in stroke recovery therapy. The first step 602 in the method generally includes flowing a target fluid to be cooled from a reservoir. The target fluid reservoir may include, for example, an IV bag containing a suitable intravenous fluid such as saline solution, and which may additionally include a therapeutically active drug if indicated for the specific situation. Alternatively, a drug may be added to the saline solution after the saline solution has exited a cooling device. The second step 604 in the method includes flowing the target fluid through a target fluid inlet and into an inner conduit(s) of the cooling device, as described above in conjunction with FIG. 5. The third step 606 in the method includes altering a reactant inlet from a closed state to an open state, as described above. As discussed above in conjunction with FIG. 5, the reactant inlet may be altered from the closed state to the open state prior to flowing the target fluid through the target fluid inlet of the cooling device, so as to allow the reaction to commence prior to the target fluid entering the inner conduit(s) of the cooling device. The fourth step 608 in the method includes flowing the target fluid through a target fluid outlet of the cooling device into a cooled-fluid-receiving tube, as described above. The fifth step 610 includes administering to the patient the target fluid in the cooled-fluid-receiving tube intravenously until, for example, a state of hypothermia is reached in the patient. Administering the cooled target fluid to the patient may include adding therapeutically active drugs to the cooled target fluid. As another example of an implementation of the present teachings, the fifth step 610 may include administering the cooled target fluid to the patient to begin induced hypothermia therapy in the pre-hospital setting, although a state of induced hypothermia in the patient may not be reached until the patient is, for example, in the in-hospital setting. As yet another example, the fifth step 610 may include intravenously administering the cooled target fluid to the patient in order to significantly reduce the core body temperature of the patient, with or without the patient ever reaching a state of hypothermia.

Figure 7:
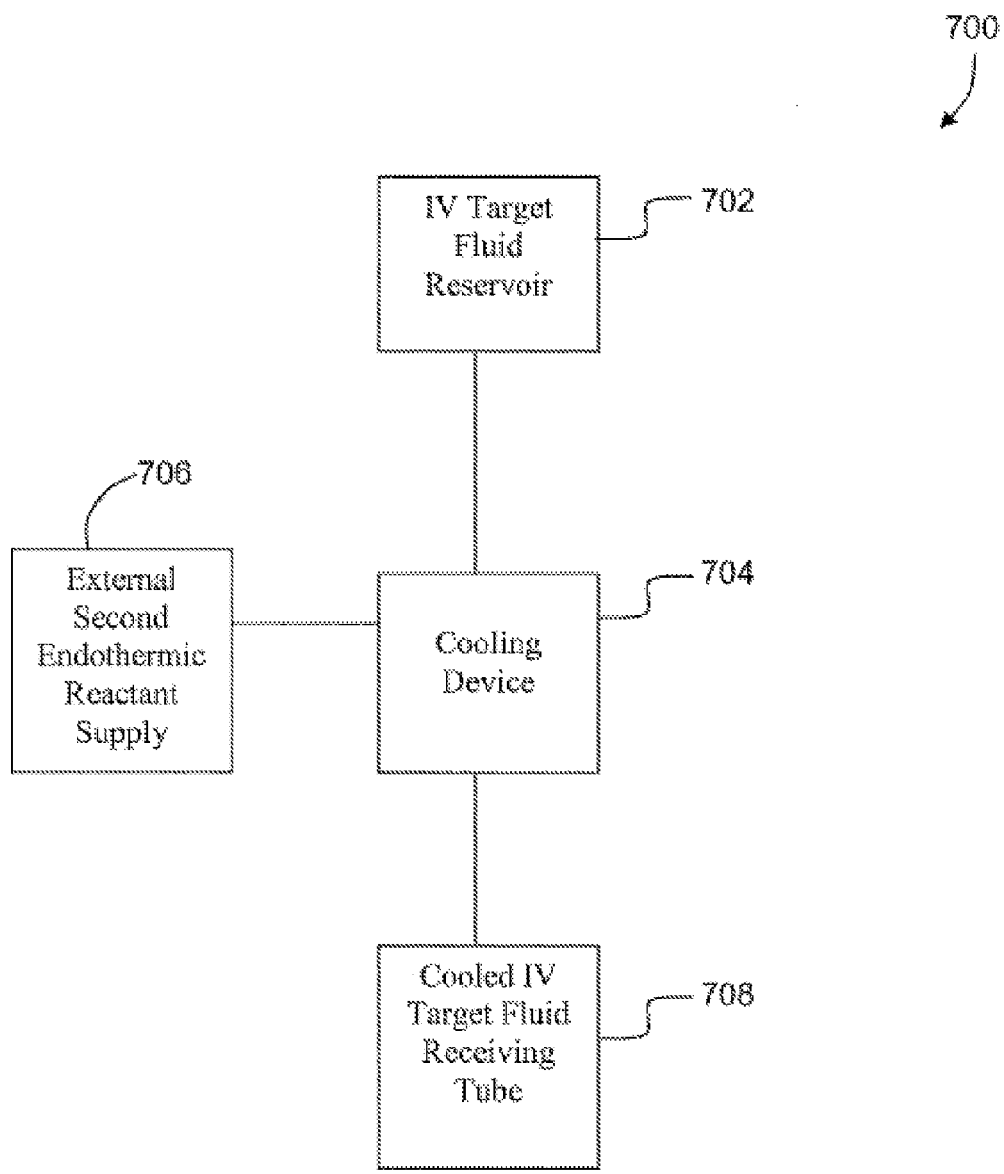
FIG. 7 is a schematic of an intravenous target fluid delivery system according to the present teachings.

FIG. 7 is a schematic of an intravenous target fluid delivery system 700 according to the present teachings. The intravenous target fluid delivery system 700 includes an IV target fluid reservoir 702, a cooling device 704, and a cooled IV target fluid receiving tube 708. The IV target fluid reservoir 702 contains an IV target fluid to be cooled in the cooling device 704. The IV target fluid reservoir 702 may include a standard IV bag, for example. The IV target fluid may include saline solution, and the saline solution may include therapeutically active drugs. The IV target fluid reservoir 702 fluidly communicates with a target fluid inlet of the cooling device 704. The target fluid inlet may generally be configured to accommodate the size of any inlet tubing or fitting that fluidly couples the IV target fluid reservoir 702 to the target fluid inlet of the cooling device 704. The cooling device 704 may generally be configured as discussed above with respect to FIGS. 1 through 4. For example, the cooling device 704 may include the target fluid inlet through which the IV target fluid to be cooled may enter the cooling device 704, and a target fluid outlet through which the cooled IV target fluid may exit the cooling device 704, the target fluid outlet being in fluid communication with the cooled IV target fluid receiving tube 708.

The cooling device 704 includes a chamber surrounding one or more inner conduits between the target fluid inlet and the target fluid outlet, and contains a first endothermic reactant. The inner conduit(s) fluidly communicates with the target fluid inlet and the target fluid outlet, and provides one or more flow paths for the IV target fluid to be cooled. The chamber includes a reactant inlet that is selectively alterable from a closed state to an open state. In the closed state, the first endothermic reactant is isolated from a second endothermic reactant and no endothermic reaction occurs. In the open state, the reactant inlet provides a flow path for enabling the second endothermic reactant to come into contact with the first endothermic reactant in the chamber for initiating the endothermic reaction and consequently cooling the IV target fluid in the inner conduit(s). In the present example, the second endothermic reactant may be flowed into the chamber via the reactant inlet by, for example, an external second endothermic reactant supply 706 (e.g., a syringe or other external source of the second endothermic reactant). Alternatively, the second endothermic reactant may be provided internally within the cooling device 704 as described above in conjunction with FIG. 4. In some implementations, the first endothermic reactant may not be preloaded in the chamber and may be flowed into the chamber via the reactant inlet by, for example, an external first endothermic reactant supply. The cooled IV target fluid receiving tube 708 is configured for intravenously administering the cooled IV target fluid to a patient. The cooled IV target fluid receiving tube 708 may include, for example, an IV catheter or any other suitable IV fluid delivery device for administering the cooled IV target fluid to the patient. Therapeutically active drugs may be added to the cooled IV target fluid prior to administering the cooled IV target fluid to the patient. The cooled IV target fluid may be utilized to reduce the core body temperature of the patient. In one example, the cooled IV target fluid may be administered to the patient until the patient reaches a state of hypothermia.

In general, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A cooling device comprising:
   a target fluid inlet;
   a target fluid outlet;
   a plurality of inner conduits fluidly communicating with the target fluid inlet and the target fluid outlet, the plurality of inner conduits providing a plurality of respective flow paths for a target fluid to be cooled; and
   a chamber surrounding the plurality of inner conduits and containing a first endothermic reactant, the chamber including a reactant inlet selectively alterable from a closed state to an open state, wherein:
      in the closed state, the first endothermic reactant is isolated from a second endothermic reactant and no endothermic reaction occurs; and
      in the open state, the reactant inlet provides a flow path for enabling the second endothermic reactant to come into contact with the first endothermic reactant in the chamber for initiating the endothermic reaction and cooling the target fluid in the plurality of inner conduits.

2. The cooling device of claim 1, wherein the reactant inlet comprises a fitting configured for connection to an external source of the second endothermic reactant.

3. The cooling device of claim 1, wherein the first endothermic reactant comprises an inorganic salt.

4. The cooling device of claim 3, wherein the second endothermic reactant comprises water.

5. The cooling device of claim 1, wherein at least a portion of each inner conduit is helical.

6. The cooling device of claim 1, wherein the reactant inlet comprises a barrier and in the closed state, the barrier divides the chamber into a first region containing the first endothermic reactant, and a second region containing the second endothermic reactant.

7. The cooling device of claim 6, further comprising an actuator configured to open the barrier wherein the reactant inlet is altered to the open state.

8. The cooling device of claim 7, wherein the actuator is configured to puncture the barrier.

9. The cooling device of claim 7, wherein the actuator is configured to move at least a portion of the barrier to create an opening therethrough.

10. An intravenous target fluid delivery system comprising:
   an IV target fluid reservoir including an IV target fluid to be cooled;
   a cooling device including:
      a target fluid inlet fluidly communicating with the IV target fluid reservoir;
      a target fluid outlet;
      a plurality of inner conduits fluidly communicating with the target fluid inlet and the target fluid outlet, the plurality of inner conduits providing a plurality of respective flow paths for the IV target fluid to be cooled; and
      a chamber surrounding the plurality of inner conduits and containing a first endothermic reactant, the chamber including a reactant inlet selectively alterable from a closed state to an open state, wherein in the closed state, the first endothermic reactant is isolated from a second endothermic reactant and no endothermic reaction occurs, and in the open state, the reactant inlet provides a flow path for enabling the second endothermic reactant to come into contact with the first endothermic reactant in the chamber for initiating the endothermic reaction and cooling the IV target fluid in the inner conduit; and
   a cooled IV target fluid receiving tube fluidly communicating with the target fluid outlet, wherein the cooled IV target fluid receiving tube is configured for intravenously administering the cooled IV target fluid to a patient.

11. The intravenous target fluid delivery system of claim 10, wherein the IV target fluid comprises saline solution.

12. The intravenous target fluid delivery system of claim 11, wherein the IV target fluid further comprises a therapeutically active drug.

13. The intravenous target fluid delivery system of claim 10, wherein the reactant inlet comprises a fitting configured for connection to an external source of the second endothermic reactant.

14. The intravenous target fluid delivery system of claim 10, wherein the reactant inlet comprises a barrier and in the closed state, the barrier divides the chamber into a first region containing the first endothermic reactant, and a second region containing the second endothermic reactant.

15. The intravenous target fluid delivery system of claim 14, further comprising an actuator configured to open the barrier wherein the reactant inlet is altered to an open state.

16. The intravenous target fluid delivery system of claim 10, wherein the cooled IV target fluid receiving tube includes an IV catheter.

* * * * *